(12) United States Patent
Lee et al.

(10) Patent No.: US 11,209,410 B2
(45) Date of Patent: Dec. 28, 2021

(54) DISSOLUTION TESTER ASSEMBLY WITH INTEGRATED IMAGING SYSTEM

(71) Applicant: Logan Instruments Corporation, Somerset, NJ (US)

(72) Inventors: Luke Lee, Belle Mead, NJ (US); Yu Sheng Zhang, Stewartsville, NJ (US); Charles Cheetham, Somerset, NJ (US)

(73) Assignee: Logan Instruments Corporation, Somerset, NJ (US)

( * ) Notice: Subject to any disclaimer, the term of this patent is extended or adjusted under 35 U.S.C. 154(b) by 1659 days.

(21) Appl. No.: 14/697,587

(22) Filed: Apr. 27, 2015

(65) Prior Publication Data

US 2015/0358587 A1 Dec. 10, 2015

Related U.S. Application Data

(60) Provisional application No. 62/010,167, filed on Jun. 10, 2014, provisional application No. 62/072,721, filed on Oct. 30, 2014.

(51) Int. Cl.
*H04N 5/00* (2011.01)
*G01N 33/15* (2006.01)
*H04N 5/225* (2006.01)

(52) U.S. Cl.
CPC ........... *G01N 33/15* (2013.01); *H04N 5/2251* (2013.01)

(58) Field of Classification Search
CPC ...... H04N 7/181; H04N 5/247; H04N 5/2251; H04N 7/18; G01N 33/15
USPC .......................................................... 348/159
See application file for complete search history.

(56) References Cited

U.S. PATENT DOCUMENTS

| | | | |
|---|---|---|---|
| 4,636,849 A | 1/1987 | Wada et al. | |
| 4,754,657 A | 7/1988 | Schneider | |
| 4,809,748 A * | 3/1989 | Robins | F16K 11/0743 137/625.11 |
| 4,855,821 A * | 8/1989 | Swon | G01N 13/00 348/89 |
| 5,816,701 A | 10/1998 | Martin et al. | |
| 6,091,453 A * | 7/2000 | Coan | H04N 5/2251 248/187.1 |
| 6,170,980 B1 * | 1/2001 | Martin | B01F 1/0011 366/144 |
| 6,174,497 B1 * | 1/2001 | Roinestad | G01N 13/00 366/142 |
| 6,336,739 B1 | 1/2002 | Lee | |

(Continued)

*Primary Examiner* — Frank F Huang
(74) *Attorney, Agent, or Firm* — Brian Roffe (57) ABSTRACT

Dissolution tester assembly that tests pharmaceutical tablets includes a frame that operatively supports a vessel having an interior into which a tablet is placed, a camera assembly supported by the frame and including a shaft having a hollow portion and an end that extends into the vessel interior, and an imaging system for imaging the tablet during the dissolution process to enable display of the images on a monitor. The imaging system includes a first camera positioned in the hollow portion of the shaft and oriented to image downward toward a bottom of the vessel, and/or a second camera positioned on the frame at a location directly below the vessel and oriented to image upward toward the bottom of the vessel. An attachment, such as a paddle for stirring or a basket for retaining the tablet, may be positioned at the end of the shaft in the vessel.

20 Claims, 6 Drawing Sheets

(56) References Cited

U.S. PATENT DOCUMENTS

| | | | |
|---|---|---|---|
| 6,535,796 B1* | 3/2003 | Sierro | G01N 11/14 700/281 |
| 7,021,163 B2 | 4/2006 | Kyne | |
| 7,131,136 B2* | 10/2006 | Monroe | G08B 13/19641 725/105 |
| 7,543,354 B2 | 6/2009 | Lee et al. | |
| 7,585,465 B2 | 9/2009 | Lee et al. | |
| 7,914,741 B2 | 3/2011 | Williams et al. | |
| 8,031,264 B2* | 10/2011 | Iwamura | H04N 7/181 348/143 |
| 8,322,193 B2 | 12/2012 | Castro et al. | |
| 8,345,094 B2* | 1/2013 | Demers | G01B 11/14 348/125 |
| 8,525,877 B2* | 9/2013 | Lortie | H04N 7/183 348/82 |
| 8,708,548 B2 | 4/2014 | Engelhardt et al. | |
| 2001/0037509 A1* | 11/2001 | Kligman | H04N 7/181 725/105 |
| 2003/0081121 A1* | 5/2003 | Kirmuss | B60R 11/02 348/143 |
| 2003/0149816 A1* | 8/2003 | Poo | G06K 19/07 710/62 |
| 2003/0234928 A1* | 12/2003 | Lucas | C23C 2/003 356/318 |
| 2004/0038169 A1* | 2/2004 | Mandelkern | A61B 1/24 433/29 |
| 2004/0145676 A1* | 7/2004 | Lin | H04N 1/00204 348/374 |
| 2005/0003550 A1* | 1/2005 | Kyne | G01N 33/15 436/2 |
| 2006/0159164 A1* | 7/2006 | Finizio | B64D 45/0015 375/240.01 |
| 2008/0036863 A1* | 2/2008 | Esbensen | G08B 13/19656 348/159 |
| 2008/0129822 A1* | 6/2008 | Clapp | H04N 5/77 348/143 |
| 2008/0297587 A1* | 12/2008 | Kurtz | G06K 9/00335 348/14.08 |
| 2009/0256908 A1* | 10/2009 | Chen | G08B 13/19641 348/143 |
| 2010/0130054 A1* | 5/2010 | Le | H01B 7/0838 439/502 |
| 2010/0198009 A1* | 8/2010 | Farr | A61B 1/00103 600/109 |
| 2011/0099095 A1* | 4/2011 | Moore | G06Q 10/063 705/30 |
| 2011/0144517 A1* | 6/2011 | Cervantes | A61B 5/08 600/538 |
| 2011/0189936 A1* | 8/2011 | Haspers | A47B 81/00 454/184 |
| 2011/0211069 A1* | 9/2011 | Sybesma | H04N 7/185 348/143 |
| 2011/0234807 A1* | 9/2011 | Jones | G08B 13/19641 348/159 |
| 2012/0075465 A1* | 3/2012 | Wengrovitz | H04N 7/181 348/143 |
| 2012/0086802 A1* | 4/2012 | Eng | A01K 61/95 348/135 |
| 2012/0281095 A1* | 11/2012 | Trenciansky | G06Q 10/00 348/159 |
| 2013/0019124 A1* | 1/2013 | Grimshaw | G06F 11/2015 714/24 |
| 2013/0061624 A1* | 3/2013 | Zwinkels | H05K 7/1497 62/259.4 |
| 2013/0078733 A1* | 3/2013 | Holmes | B01L 3/0217 436/174 |
| 2016/0091779 A1* | 3/2016 | Jodoin | G03B 17/561 396/428 |
| 2016/0134737 A1* | 5/2016 | Pulletikurty | G06F 3/0227 715/735 |
| 2017/0001577 A1* | 1/2017 | Seagraves | G03B 17/561 |

* cited by examiner

DISSOLUTION TESTER ASSEMBLY WITH INTEGRATED IMAGING SYSTEM

CROSS REFERENCE TO RELATED APPLICATIONS

This application claims priority to U.S. provisional patent application Ser. Nos. 62/010,167 filed Jun. 10, 2014 and 62/072,721 filed Oct. 30, 2014, both of which are incorporated by reference herein.

FIELD OF THE INVENTION

The present invention relates generally to a system for imaging a pharmaceutical tablet during its dissolution during testing, and more particularly to a system that enables visualization of the manner in which a pharmaceutical tablet breaks downs and dissolves in a vessel used in a dissolution tester.

BACKGROUND OF THE INVENTION

Viewing a pharmaceutical tablet dissolving in a dissolution vessel is not easy. When using a water bath type dissolution testing system, scientists or other testing personnel have to see through a wall of a water tank of the dissolution tester, water in the tank, a wall of the glass vessel in which the tablet is dissolving and the tablet. With all kinds of illusions and distortions, an external camera cannot see well or record the tablet dissolving process.

Nonetheless, it is very important to know how the tablet breaks down in each stage of dissolution and visualize the dissolution clearly. Current external camera systems are not able to accomplish this requirement.

SUMMARY OF THE INVENTION

A dissolution tester assembly in accordance with the invention includes a frame that operatively supports a vessel having an interior into which a tablet is placed for testing dissolution of the tablet, a shaft having an attachment at an end of the shaft that extends into the interior of the vessel, and an integral imaging system that images dissolution of the tablet. In one embodiment, the imaging system includes a first camera positioned in a hollow portion of the shaft and oriented to image downward toward a bottom of the vessel. Additionally, or alternatively, the imaging system includes a second camera positioned on the frame at a position directly below or underneath the vessel and oriented to image upward toward the bottom of the vessel when supported by the frame.

During use, the first and second cameras, when both are present, image a tablet dissolving at the bottom of the vessel from both above and below the tablet. The images may be displayed on a monitor coupled to the cameras. The imaging process may be controlled by a control unit coupled to the cameras, and to the monitor. The control unit may include a recording unit that records images obtained by the first and second cameras.

Integration of the first camera may involve arranging a tube in the hollow portion of the shaft and mounting the first camera into the tube. A disk of transparent material, such as glass, is arranged below the first camera to secure the first camera against damage by the solution in the vessel.

The frame may be used for a water bath type dissolution testing system or an air bath type dissolution testing system. In the latter case, the frame defines an air chamber partly or substantially surrounding the vessel when the vessel is supported by the frame, and the second camera images upward toward the bottom of the vessel through an air chamber defined by the frame. Use of an air bath type dissolution testing system is therefore advantageous over a water bath type dissolution testing system because the camera imaging from below has only the wall defining the vessel between it and the tablet that is dissolving. The water bath type dissolution testing system also has liquid between the camera and the wall defining the vessel.

Another embodiment of a dissolution testing assembly in accordance with the invention includes a frame, a plurality of removable vessels supported by the frame, each having an interior into which a tablet is placed for testing dissolution of the tablet, and a plurality of camera assemblies supported by the frame. Each camera assembly includes a shaft having a hollow portion and an attachment at an end of the shaft that extends into the interior of a respective vessel when supported by the frame. An imaging system is associated with the frame and includes a plurality of first cameras positioned in the hollow portion of the shafts of the camera assemblies and oriented to image downward toward a bottom of the respective vessel when supported by the frame, and/or a second camera positioned on the frame at a location directly below or underneath the respective vessel when supported by the frame and oriented to image upward toward the bottom of the respective vessel. Thus, a dissolution tester assembly may include only the first cameras integrated into the camera assemblies, or only the second cameras fixed to the frame, or both. When both are present, the first and second cameras image a tablet dissolving at the bottom of the vessels. The attachment may be a paddle for stirring the solution in the vessel or a basket with a mesh periphery that retains the tablet.

Other and further objects, advantages and features of the present invention will be understood by reference to the following specification in conjunction with the annexed drawings.

BRIEF DESCRIPTION OF THE DRAWINGS

The invention, together with further objects and advantages thereof, may best be understood by reference to the following description taken in conjunction with the accompanying drawings wherein like reference numerals identify like elements.

DETAILED DESCRIPTION OF THE INVENTION

Figure 1:
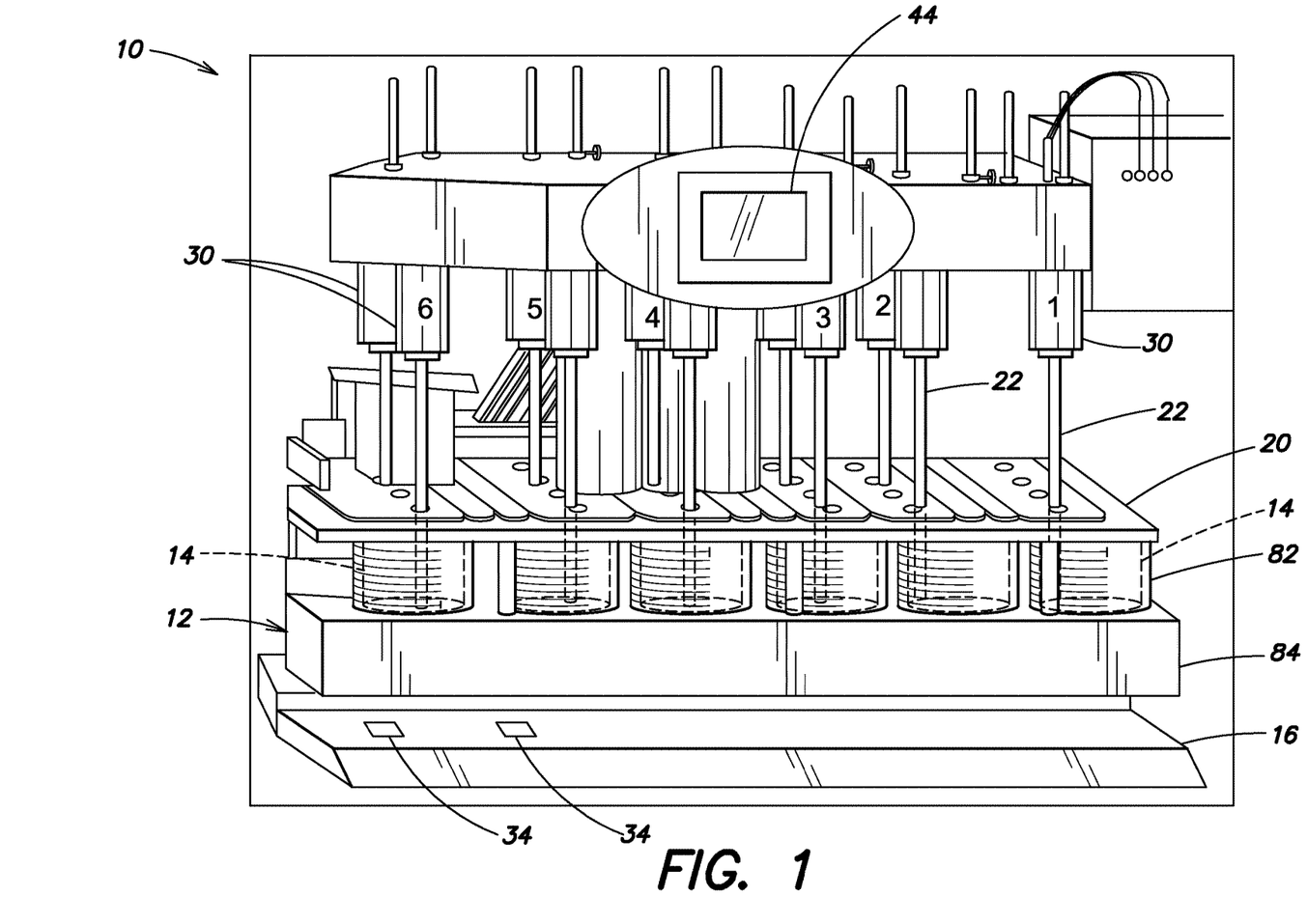
FIG. 1 is a perspective view of an air bath dissolution tester assembly including an integrated imaging or camera system in accordance with the invention.
Figure 2:
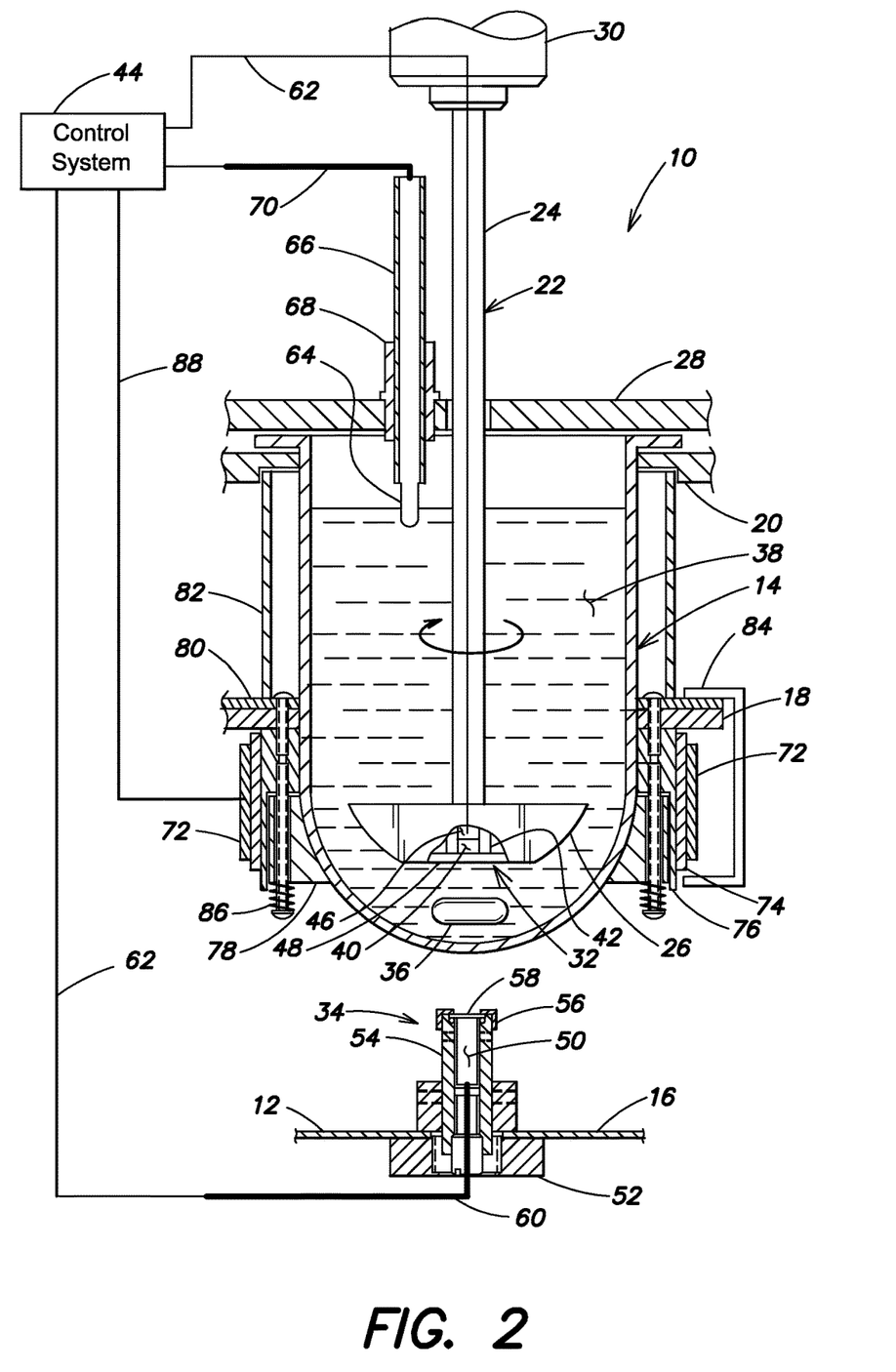
FIG. 2 is a cross-sectional view of one of the dissolution vessels of the air bath dissolution tester assembly including an integrated imaging or camera system shown in FIG. 1.
Figure 3:
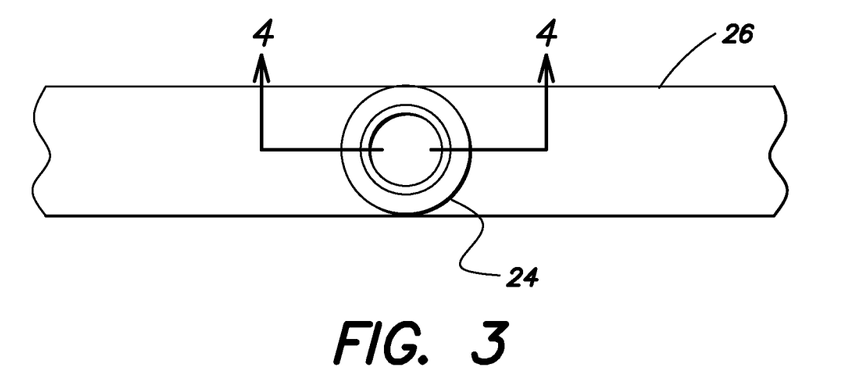
FIG. 3 is a view taken along the line 3-3 of FIG. 2.

Referring to the accompanying drawings wherein like reference numerals refer to the same or similar elements, FIGS. 1 and 2 show an air bath dissolution tester assembly having an integrated imaging system of the present invention, designated generally as 10. The dissolution tester assembly 10 includes a frame 12 that typically supports a plurality of dissolution testing vessels 14. The frame 12 includes a bottom plate 16, an intermediate support plate 18 and a vessel plate 20 for supporting the vessels 14. Frame 12 may have substantially the same features as a unit designated the UDT-814 sold by the applicant, Logan Instruments Corp. of Somerset, N.J. This unit is designed to accommodate up to twelve dissolution testing vessels.

For each vessel 14, the tester assembly 10 includes a paddle shaft assembly 22 supported on the frame 12. Paddle shaft assembly 22 includes a shaft 24 and a paddle 26 on a portion or at an end of the shaft 24 that will be operatively situated in the vessel 14. However, the shaft 24 may alternatively be connected to a basket as described below with reference to FIGS. 5 and 6. In both embodiments, the shaft 24 passes through a cover 28 on the vessel 14. A partially internal mounting assembly 30 couples the shaft 24 to the frame 12 and allows for controlled rotation of the shaft 24 relative to the frame 12 (See FIGS. 1 and 2).

The frame 12 is integrated with camera assemblies 32, 34 that image and enable recordation of the dissolving process of a tablet 36 in an aqueous solution 38 in the vessel 14 from locations significantly closer to the tablet 36 than prior art camera systems, such as the LabEye Digital Video System for dissolution testing monitoring and recording, by Distek, Inc. Camera assemblies 32, 34 are thus integral or built-in with the frame 12 or parts thereof.

Specifically, camera assemblies 32 image the dissolution of the tablet 36 from a location above the tablet 36 while camera assembles 34 image the dissolution of the tablet 36 from a location below the tablet 36.

Figure 4:
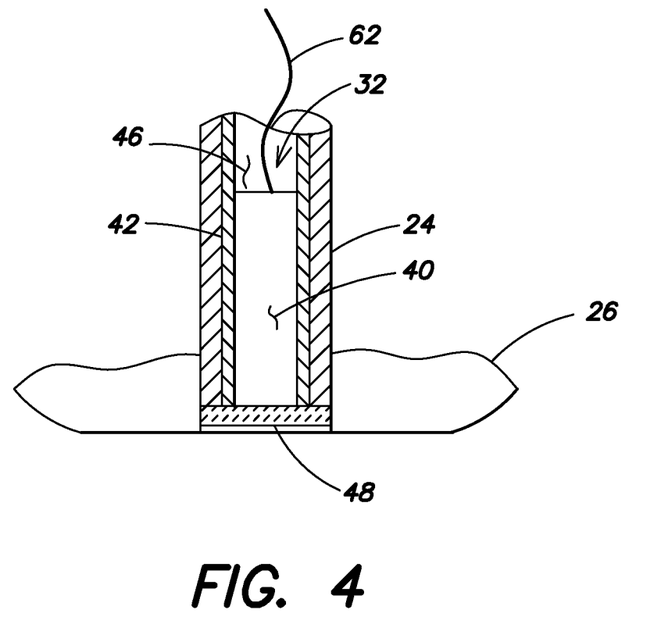
FIG. 4 is a cross-sectional view taken along the line 4-4 in FIG. 3.

Each camera assembly 32 is positioned to enable video recordation of the tablet dissolution process from a location above a tablet 36 that is usually positioned at the bottom of the vessel 14. To this end, each camera assembly 32 includes a miniature camera 40 mounted into a tube 42 and having an imaging inlet oriented downward. The camera 40 may thus be referred to as a top camera. This camera assembly 32 is placed into a hollow interior 46 of the shaft 24 (see FIG. 4). The bottom of the shaft 24 is sealed with a glass disk 48, which allows the camera 40 to see through to the tablet 36, and stops the acid media in the vessel 14 from damaging the camera 40 (see FIG. 4). Instead of a glass disk 48, a disk of another transparent material that will withstand the effects of the dissolution process may also be used. The paddle 26 stays on top of the tablet 36, preferably within about 1 inch, which thereby provides a very close view of the dissolution of the tablet 36 from above.

On the opposite side of the tablet 36, each camera assembly 34 comprises a miniature camera 50 mounted on the frame 12 at a location under the dissolution vessel 14, specifically, directly underneath a location at which the tablet 36 is likely to rest in the dissolution vessel 14. The camera assemblies 34 may be mounted on the bottom plate 16 by means of a mount nut 52.

This directly below or directly underneath position of the camera 50 means that there is no interposing structure between the camera 50 and the bottom of the vessel 14. Since the vessel 14 is usually made of transparent glass, the camera 50 will have a very clear, unobstructed view of the tablet 36 from below. It is possible for the camera 50 not to be directly below or directly underneath the tablet 36 in the vessel 14, i.e., not directly below or directly underneath the lowest part of the vessel 14, and slightly offset from an axis in line with the lowest part of the vessel 14. However, the position of the camera 50 directly below or directly underneath the lowest part of the vessel 14 is a preferred embodiment since the tablet 36 will generally lie in the lowest part of the vessel 14.

The camera 50, also referred to as a bottom camera, is preferably mounted in a tube 54 that may be fixed to the bottom plate 16 of the frame 12 and/or integrated into the frame 12. The camera 50 faces up, i.e., has an imaging inlet oriented upward, to record the dissolution process of the tablet 36 from below. The position of camera 50 is therefore preferably at or below the lowermost point of the vessel 14.

A cap with a seal 56 overlies the camera 50 and a lens cover 58 covers the imaging unit of the camera 50. A cable 60 leads from the camera 50 through the tube 54 to a display, monitor and/or control system represented generally as 44 (see FIG. 1). Similarly, camera 40 is coupled through the shaft 24 via a cable 62 to the same control system 44.

Once positioned, the camera 50 in its tube 54 is fixed under the vessel 14. In an exemplifying use for a twelve-vessel dissolution tester, there are twelve bottom cameras 50 on the bottom plate 16. Each bottom camera 50 is thus at a fixed position and immovable by means of the mounting tube 54 to the bottom plate 16. However, to address the possibility of the use of different vessels, the position of the bottom cameras 50 may be changed for different vessels 14. An adjustable positioning structure for camera 50 is therefore possible to enable its position to be moved for different vessels 14.

Additional structure of the tester assembly 10 includes structure that supports the vessels 14 and provides for the generation of an air bath. Specifically, the tester assembly 10 includes, for each vessel 14, a temperature sensor 64 adapted to extend into the interior of the vessel 14, and that is supported by a sensor sleeve 66, and a sensor holder 68 on the vessel cover 28. A cable 70 connects the sensor 64 to the control system 44. A heater 72 provides thermal energy through a heater plate 74, a heater block 76 and a heating bowl 78 to the vessel 14. Thermal insulation 80 aids in maintaining the appropriate heat for the vessel 14. Heater 72 is coupled to the control system via a cable 88. Clear insulation 82 enables the contents of the vessels 14 to be visible. A protective shield 84 is preferably provided around the heater 72. Springs 86 may be used to keep the heater bowl 78 in contact with the outer surface of the vessel 14. The heating block 76 is thus outside the vessel 14, while the spring-loaded heating bowl 78 is around the vessel 14, with the result that heat is transferred from both components to the vessel 14. Alternative heating mechanisms may be used in the invention to provide heat to the vessel 14 in a manner to form an air bath for the vessel 14.

Figure 5:
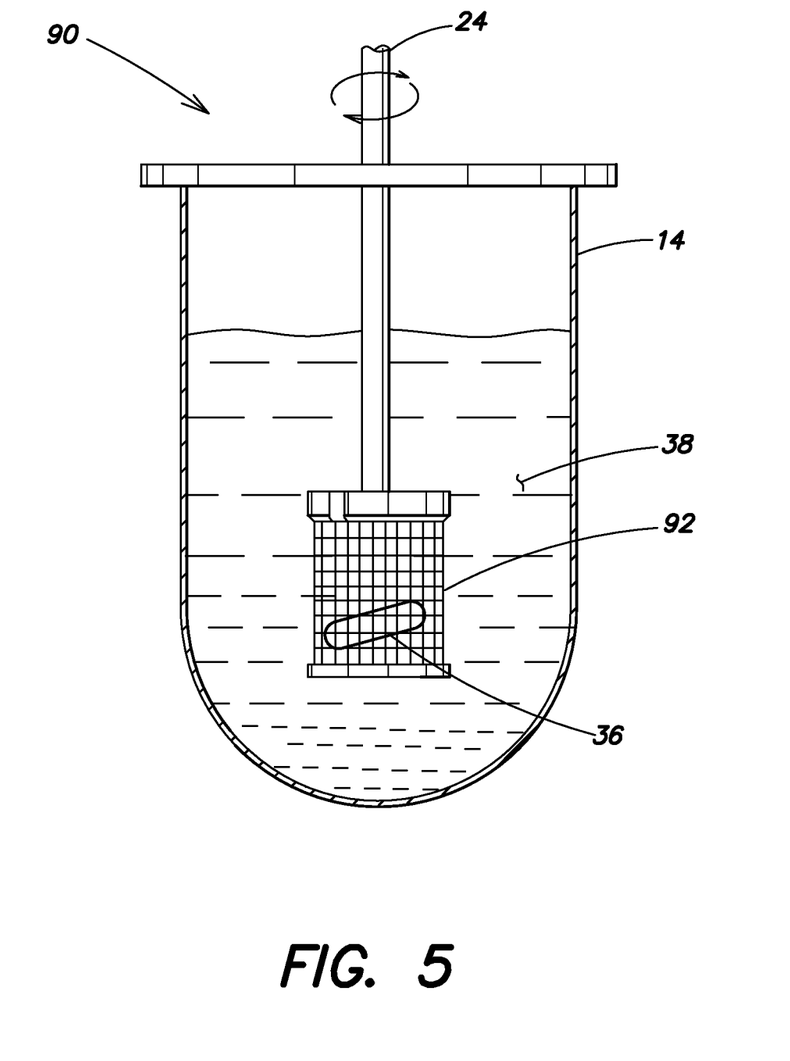
FIG. 5 is a perspective view of a second embodiment of a camera assembly in accordance with the invention for use in a dissolution tester in accordance with the invention.
Figure 6:
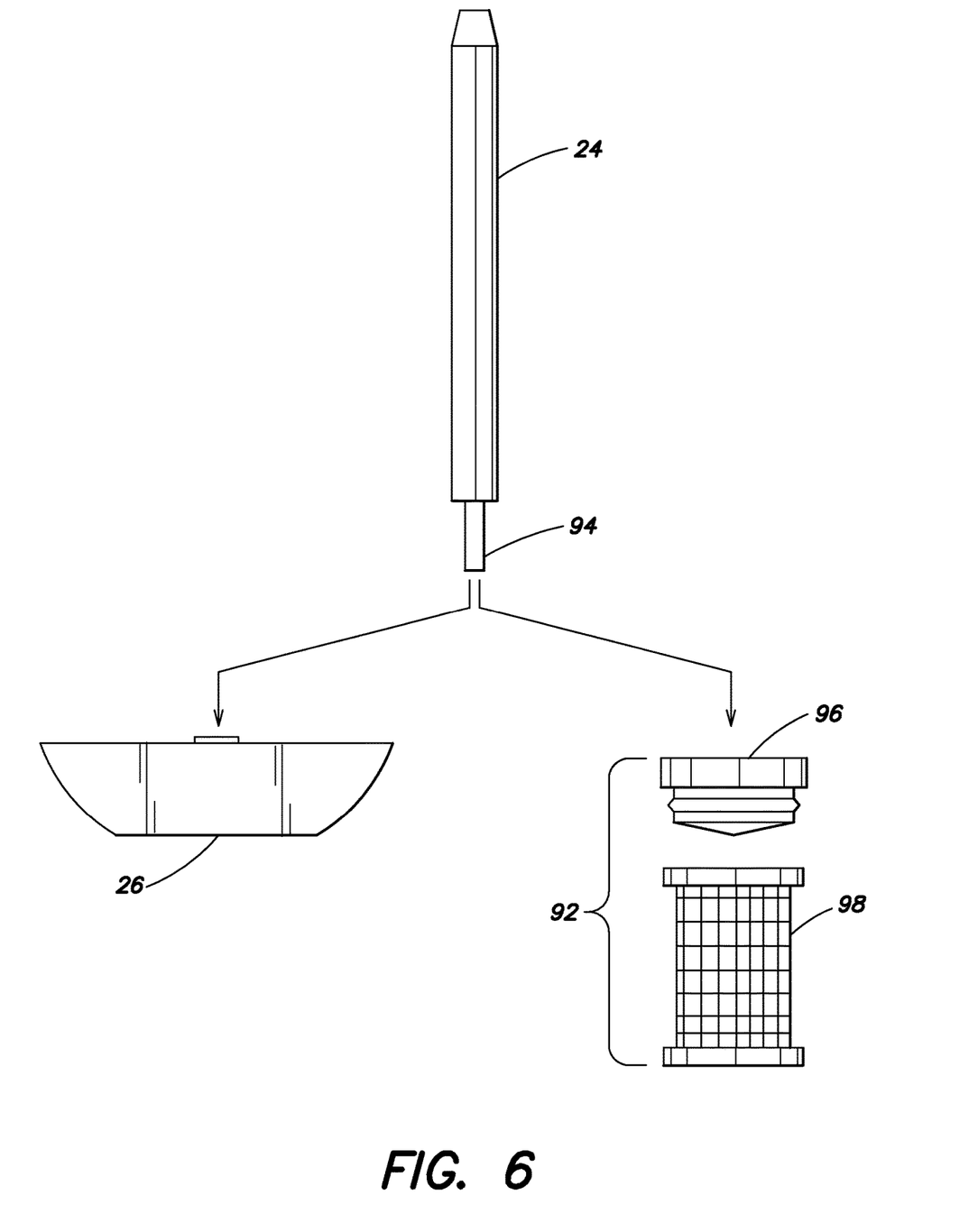
FIG. 6 is a view showing the alternative use of a camera shaft with either a paddle attachment or a basket attachment for the dissolution tester in accordance with the invention.

Referring now to FIGS. 5 and 6, another embodiment of a camera assembly in accordance with the invention is designated generally as 90 and includes the shaft 24 and a basket 92 attached to or near the end of the shaft 24 that will be positioned in the dissolution vessel 14. As such, the shaft 24 is considered a basket shaft as opposed to a paddle shaft which is the case when the attachment at the end of the shaft 24 is a paddle 26. Generally, the basket 92 allows the solution in the vessel 14 to pass through apertures in its wall or walls into contact with the tablet 36.

The camera assembly 32 allows imaging of the dissolution of a tablet 36, dosage form, etc. that has been placed in the basket 92 for dissolution testing with imaging (see FIG. 5). The shaft 24 may include the same structure described above, i.e., an in-shaft camera such as camera 40 mounted into the tube 42 that is placed into a hollow interior 46 of the shaft 24 (see FIG. 4). Thus, the same shaft 24 may be used with a paddle 26 or with a basket 92, and will be referred to herein as a camera shaft. The camera shaft may be designed to alternately engage with a paddle 26 or a basket 92 (or even possibly another attachment), depending on the desired use. To this end, the end of the shaft 24 may have an attachment mechanism 94 that mates with a cooperating attachment mechanism on the paddle 26 and the basket 92, e.g., threads.

The bottom of the shaft 24 is sealed with the glass disk 48 and the basket 92 is attached to the shaft 24 to provide visualization of the interior of the basket 92, and enable recording of, for example, the tablet dissolution. In this manner, the camera 40 visualizes the tablet 36 in the basket 92 through the disk 48. This system may be used for dissolution testing of a variety of pharmaceutical products including tablets and capsules, for which stirring is not required. For example, the basket 92 is useful for solids, floaters, beads, modified release products and surfactants in media.

The basket 92 may include a basket head or head part 96 that is attached to the shaft 24 and a cage 98 that is removably attachable to the basket head 96, e.g., by threads (see FIG. 6). The cage 98 may be selected with characteristics (mesh size and cage volume) within ranges that would be readily determinable by skilled in the art to which this invention pertains in view of the disclosure herein. For example, a mesh size of 40 is possible, as well as a mesh size in the range of about 10 mesh to about 100 mesh. A volume of the basket cage 98 may be about 900 ml, but could be in a range of about 100 ml to about 4000 ml. The material from which the basket 92 is made, e.g., stainless steel, and the manner in which it is attached to the shaft 24 would also be readily ascertainable by those skilled in the art in view of the disclosure herein.

Another aspect of the invention is therefore the camera assemblies 32 or the camera shaft. Each camera assembly 32 includes the shaft 24 having the hollow interior and the tube 42 in which the camera 40 is mounted. The camera assembly 32 is then attached to the frame 12 of the dissolution tester 10 and can be used by mounting an attachment, such as the paddle 26 or the basket 92, onto the lower end of the shaft 24. The electronic, electrical and/or data communications from the camera 40 the processing hardware is partly provided in the camera assemblies 32.

An advantage of the dissolution tester assembly 10 is that it enables testing personnel and others to more clearly view a tablet during its dissolution.

An imaging portion of the imaging system (a combination of cameras 40, 50) may be provided to each dissolution testing location on the frame 12, i.e., for each vessel 14. Thus, if there are three dissolution testing locations defined by the dissolution tester assembly 10, there would be three imaging portions for the imaging system. If there are six dissolution testing locations defined by the dissolution tester assembly 10, there would be six imaging portions of the imaging system. However, although there would be three or six separate imaging portions of the imaging system, one for each vessel 14, in an embodiment of the invention, there are common elements for all of the imaging portions, such as the control elements (control system 44) and imaging processing elements.

Another way to view the imaging portion of the imaging system is as an arrangement of two cameras that face one another in a vertical orientation to thereby image a tablet when present therebetween from two directions. Camera 40 is vertically above the tablet 36 while camera 50 is vertically below or underneath the tablet 36. Different structure for supporting the cameras 40, 50 to provide for this vertical spacing relative to the tablet 36 may also be used without deviating from the scope of the invention. Such structure should be considered encompassed within the terms camera support structure or camera support means as used herein.

In general, the structure of the frame 12 to support cameras 40, 50 and vessels 14 to enable dissolution testing is known or readily ascertainable to those skilled in the art. Additional details therefore will not be provided of the manner in which the cameras 40, 50 are controlled to stir a solution in the vessel 14 for the purpose of assessing the dissolution of a pharmaceutical tablet in a solution in the vessel 14. Moreover, details of the manner in which dissolution testing is performed using the dissolution tester assembly 10 will not be provided as they are readily understood by those skilled in the art to which this invention pertains.

In an exemplifying, non-limiting use, the vessels 14 are placed onto the vessel plate 20, liquid is placed into the vessels 14, and then the tablets 36 are placed, e.g., one in each vessel 14. The cover 28 is placed onto each vessel 14. The respective sensor 64 is inserted into contact with the liquid in each vessel 14. The control system 44 previously activates the heater 72 to heat the heater block 76 and the heater bowl 78 and monitors the temperature of the liquid or aqueous solution 38 by means of the sensor 64 and adjusts the heater 72 to maintain a desired temperature. The cameras 40, 50 are controlled by the control system 44 to image and/or record the dissolution of the tablets 36 in the vessels 14. The images and/or video may be viewed on the display or monitor portion of the control system 44 (see FIG. 1).

Figure 7:
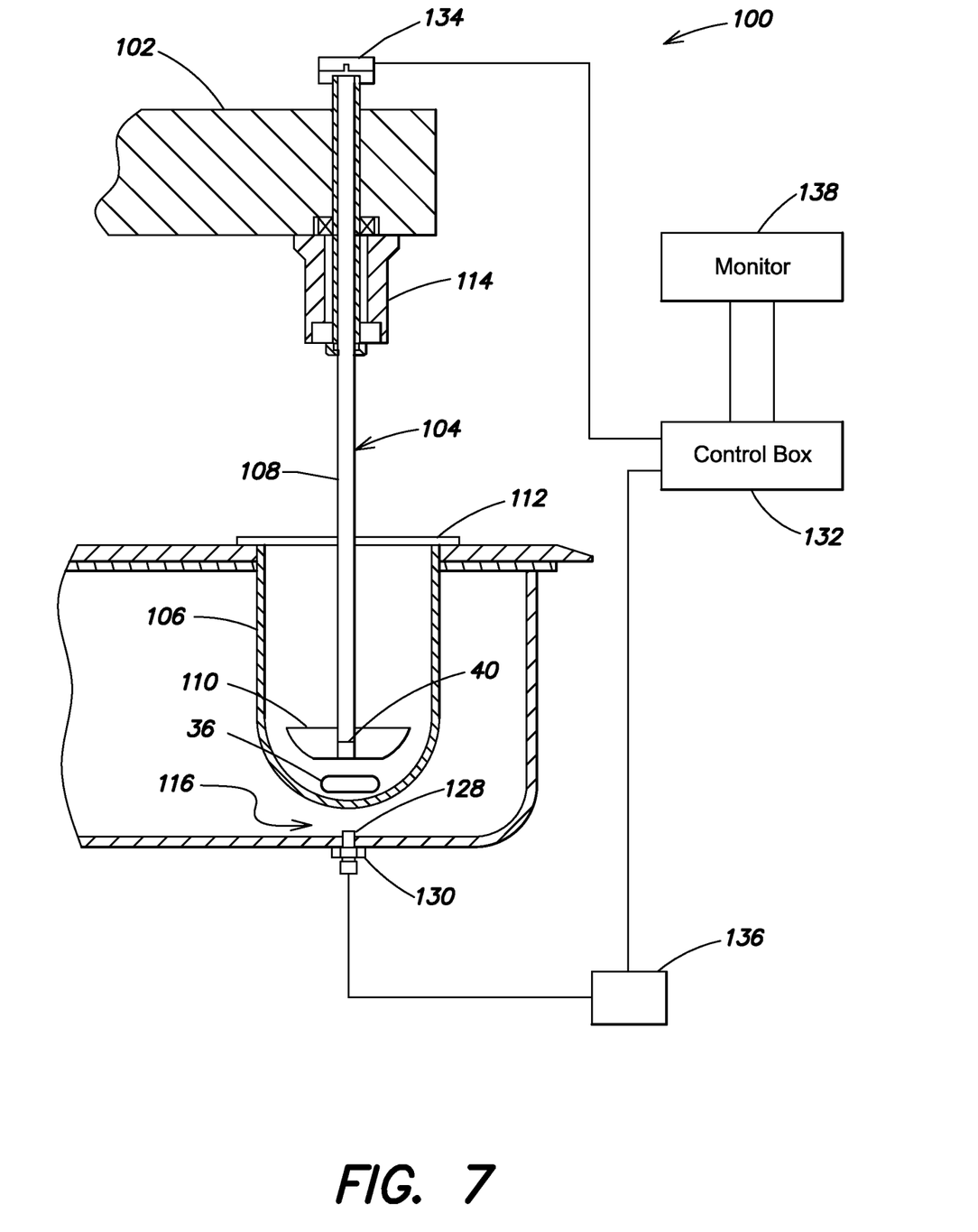
FIG. 7 is a schematic of another exemplifying, non-limiting embodiment of a dissolution tester including an integrated imaging or camera system in accordance with the invention.

FIG. 7 shows parts of a dissolution tester assembly 100 including an integrated imaging or camera system in accordance with the invention. The dissolution tester assembly 100 includes a frame 102 that typically supports a plurality of camera assemblies 104, only one of which is shown, and a plurality of dissolution testing vessels 106, only one of which is shown. The frame 102 may have any shape and form known to those skilled in the art, including and in particular, those manufactured and sold by the assignee, Logan Instruments Corporation. A dissolution tester may also be considered an invention and includes the frame 102 and one or more camera assemblies 104, i.e., the vessels 106 are not required to be considered part of the dissolution tester when sold, although such a dissolution tester cannot be used without one or more vessels.

The camera assembly 104 includes a shaft 108 supported on the frame 102. When the camera assembly 104 is used as a stirrer or stirrer assembly, it also includes a paddle 110 on a portion or at an end situated in the vessel 106. In this case, a paddle shaft is formed. However, the shaft 108 may alternatively be connected to a basket as described above with reference to FIGS. 5 and 6. In both embodiments, the shaft 108 passes through a cover 112 on the vessel 106. A mounting assembly 114 couples the shaft 108 to the frame 102 and allows for controlled rotation of the shaft 108 relative to the frame 102.

The frame 102 is integrated with an imaging system 116 that sees and enables recordation of the tablet dissolving process from locations significantly closer to the tablet than prior art camera systems. Imaging system 116 is thus integral or built-in with the frame 102 or parts thereof, e.g., the camera assembly 104.

Imaging system 116 is positioned to video record the tablet dissolution process from a location above a tablet 36 that is usually positioned at the bottom of the vessel 106, and as well as from a location directly below the tablet 36. More specifically, with respect to the imaging from the location above the tablet 36, each imaging portion includes a camera assembly 32 as described above.

With respect to the imaging from a location below the tablet 36, each imaging portion also includes another miniature camera 128 mounted on the frame 102 at a location under the dissolution vessel 106, specifically, directly below or underneath the tablet 36 in the dissolution vessel 106. This directly below or directly underneath position of the camera 128 means that there is no interposing structure between the camera 128 and the bottom of the vessel 106. Since the vessel 106 is usually made of transparent glass, the camera 128 will have a very clear, unobstructed view of the tablet 36 from below. It is possible for the camera 128 not to be directly below or directly underneath the tablet 36 in the vessel 106, i.e., not directly below or directly underneath the lowest part of the vessel 106, and slightly offset from an axis in line with the lowest part of the vessel 106. However, the position of the camera 128 directly below or directly underneath the lowest part of the vessel 106 is a preferred embodiment since the tablet 36 will generally lie in the lowest part of the vessel 106.

The camera 128, also referred to as a bottom camera, is preferably mounted in a tube, e.g., in a waterproof manner when a water bath is used. This mounting tube may be fixed to the frame 102 and/or integrated into the frame 102. The camera 128 faces up, i.e., has an imaging inlet oriented upward, to record the dissolution process of the tablet 36 from below. The position of camera 128 is therefore at the lowermost point of the vessel 106. A mounting structure 130 mounts the camera 128 to the frame 102 (see FIG. 2).

Once positioned, the camera 128 in its tube is fixed under the vessel 106. To address the possibility of the use of different vessels, the position of the bottom camera 128 may be changed for different vessels 106. An adjustable positioning structure for camera 128 is therefore possible to enable its position to be moved for different vessels 106.

Referring back to FIG. 7, the cameras 40, 128 are coupled to a control unit, control box or unit 132 via wires and image control units 134, 136. Other coupling techniques for coupling the cameras 40, 128 to the control unit 132 are also envisioned as being within the scope of the invention. Control unit 132 may include an LCD touch screen that enables paddle speed, vessel temperature and dissolution testing time control for the dissolution process. The control unit 132 is coupled to a monitor 138 on which the images from cameras 40, 128 are displayed.

Control unit 132 may also include equipment to record the dissolution of the tablet 36. This recording equipment housed in the control unit 132 would be started and stopped by the user accessing a user interface of the control unit 132, e.g., the touch screen thereof, and enable playback to allow for review of the tablet dissolution process.

Another embodiment of a dissolution tester assembly includes a dissolution tester having a cylindrical warm air bath or jacket and a dissolution vessel. The air bath or jacket may be provided by any known structure that has a frame and structure that provides a circulating air stream therein. The dissolution vessel is generally cylindrical, having a rounded bottom and an upper outwardly extending lip which is so configured as to rest on the upper end of the frame that provides the air jacket. A temperature sensor, such as a thermocouple, may be attached to the dissolution vessel by any appropriate means, such as a rubber adhesive patch, so as to insure intimate contact between the outer surface of the dissolution vessel and the temperature sensor.

A rotatable shaft is axially located within the dissolution vessel and supports the paddle agitator mounted at its lower end. The upper mounting of the shaft may be as described above for shaft 24. An electrical heating element is located within a hollow portion of the rotatable shaft and is provided with electrical power by electrical conduits controlled by a control unit. The control unit activates the heating element in response to a signal from the temperature sensor so as to allow the heating of test solution to a temperature of, for example, 37° C., and then maintain that temperature throughout the dissolution test.

In operation for dissolution testing, test solution is added to the dissolution vessel suspended by the air jacket, and electrical power is supplied to the heating element in rotating shaft, which drives the agitator paddle until the solution is brought up to temperature, e.g., 37° C. Warm air is directed upward into the air jacket, surrounding the test dissolution vessel. During this period, the test solution is degassed by the direct heat of the shaft and the agitation of agitator paddle. A tablet to be tested is dropped into the vessel and the time elapsed until complete dissolution of the tablet into the test solution is measured. The heat supplied to the heating element during the dissolution test is controlled by the control unit in a known manner in response to the temperature measured by the temperature sensor to maintain the solution at the required 37° C. temperature. Temperature data may be taken and recorded by the control as desired. The air jacket and the dissolution vessel are preferably made from a transparent material, such as glass, so the dissolution of the tablet may be observed. The air bath dissolution tester assembly includes an imaging system that allows for recordation of the dissolution process, whether from below the tablet 36, above the tablet 36 or both.

Additional features of the dissolution tester assembly 10, 100 include those of models designated UDT-804 and UDT-814 manufactured by Logan Instruments, the current assignee, to the extent practical. Additional features of the dissolution tester assembly 10 also include those disclosed in U.S. Pat. No. 6,336,739, incorporated by reference herein.

Additional patented products by the current assignee include those disclosed in U.S. Pat. No. 7,543,354 issued Jun. 9, 2009, U.S. Pat. No. 7,585,465 issued Sep. 8, 2009 and U.S. Pat. No. 8,322,193 issued Dec. 4, 2013, all of which are incorporated by reference herein. The components, methods, arrangements, systems and techniques disclosed in these patents may be used in combination with any and all of the embodiments of the invention disclosed herein, to the extent possible and/or desired. Such combinations are considered part of the invention.

An important difference between earlier dissolution testers and the present invention relates to the shaft assembly 22. Whereas the shaft in earlier dissolution testers have a solid shaft, e.g., solid SS 316 bars, the shaft assembly 22 of a dissolution tester in accordance with any of the embodiments of the invention disclosed herein may be formed or otherwise provided with a hollow interior or section 46 to enable it to accommodate the camera 40 and its mounting tube 42 (see FIG. 4). Hollow section 46 may have a size just sufficient to accommodate the camera 40 and its mounting tube 42 or extend for a longer length of the shaft 24, depending on, for example, manufacturing considerations. It may be possible to have the entire shaft 24 as a tubular piece with the camera 40 and mounting tube 42 dimensioned to fit therein with no or minimal clearance. Also, camera 40 may be mounted in a structure other than a mounting tube, or directly in the hollow section 46.

The innovative imaging system may be provided as an optional embodiment for a dissolution tester, e.g., those sold by the current assignee. For example, it is possible to construct a dissolution tester with only the top camera 40 by providing the specially constructed shafts 24 for each vessel mounting location. Cameras 50 would not be included on the frame 12 of such a dissolution tester. For such a system, there would only be imaging of the tablet 36 from above.

On the other hand, it is possible to construct a dissolution tester with conventional solid paddle shafts and with the bottom cameras 50 mounted on the frame 12 for each vessel mounting location. Thus, cameras 40 would not be included on the paddle shafts of such a dissolution tester. For such a system, there would only be imaging of the tablet 36 from below.

Then, obviously, it is possible to provide a dissolution tester as described above and shown in FIG. 7, i.e., with the specially constructed shafts 24 for each vessel mounting location and with the bottom cameras 128 mounted on the frame 102 for each vessel mounting location. For such a system, there would be imaging of the tablet 36 from both above and below.

As an alternative to integrating the imaging system described above with the UDT-814, the imaging system may be integrated with another air bath dissolution tester assembly, and the invention is not limited to any specific air bath dissolution tester assembly, and in particular, not limited to those manufactured and sold by the applicant. A dissolution tester may also be considered an invention and includes the frame 12 and the imaging system, i.e., the vessels 14 are not required to be considered part of the dissolution tester when sold, although such a dissolution tester cannot be used without one or more vessels.

There is no known dissolution tester with a built-in camera system having the features of the dissolution tester assemblies described herein, e.g., one that can image from below or underneath a vessel and/or from above or on top of the table. Although it has been tried to use a digital cameras to mount on the side of the vessels to see tablets dissolution, only images from the side of the vessel are obtained. Placement of an imaging apparatus in a shaft that is at least partly immersed in the interiors of the vessels or below the vessels as described above is believed to be novel and provides advantages of being able to visualize and record dissolution of a tablet directly above (e.g., for a tablet in a basket) or directly below, under or underneath (e.g., for a tablet under the paddle).

While particular embodiments of the invention have been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

The invention claimed is:

1. A dissolution tester, comprising:
    a frame that operatively supports a vessel having an interior into which a tablet is placed for testing dissolution of the tablet;
    a shaft having an end that extends into the interior of the vessel when the vessel is supported by said frame; and
    an integral imaging system having a first camera on said shaft oriented to image downward through a bottom of said shaft in order to obtain images of an area below said shaft and between said shaft and the vessel when supported by said frame.

2. The tester of claim 1, wherein said frame defines an air bath for the vessel.

3. The tester of claim 1, wherein said integral imaging system further comprises a tube arranged in a hollow portion of said shaft, said first camera being mounted into said tube such that said first camera is in said hollow portion of said shaft, said first camera imaging the area below said shaft and between said shaft and the vessel when supported by said frame from a position of said first camera in said hollow portion of said shaft.

4. The tester of claim 3, further comprising a disk of transparent material arranged on said shaft below said first camera, said disk of transparent material forming part of the bottom of said shaft such that said first camera obtains images of the area below said shaft and between said shaft and the vessel when supported by said frame through said disk of transparent material.

5. The tester of claim 1, further comprising a control unit coupled to said integral imaging system for controlling imaging by said integral imaging system.

6. The tester of claim 5, wherein said control unit includes a recording unit that records images being obtained by said integral imaging system.

7. The tester of claim 1, further comprising a monitor coupled to said integral imaging system for displaying images obtained by said integral imaging system.

8. The tester of claim 1, wherein said frame is configured to operatively support a plurality of additional vessels each having an interior into which a tablet is placed for testing dissolution of the tablet, further comprising:
    a plurality of additional shafts each having an end that extends into the interior of a respective one of the additional vessels when the respective additional vessel is supported by said frame; and
    a plurality of additional integral imaging system each having a first camera on a respective one of said additional shafts that is oriented to image downward through a bottom of the respective one of said additional shafts in order to obtain images of an area below the respective one of said additional shafts and between the respective one of said additional shafts and the additional vessel when supported by said frame.

9. The tester of claim 1, further comprising a paddle attached to the end of said shaft that extends into the interior of the vessel when the vessel is supported by said frame.

10. The tester of claim 1, further comprising a basket attached to the end of said shaft that extends into the interior of the vessel when the vessel is supported by said frame.

11. The tester of claim 10, wherein said basket comprises a head part attached to said shaft and a basket cage removably attached to said head part and defining an interior in which the tablet is placed for dissolution testing.

12. The tester of claim 1, further comprising:
    a temperature sensor that provides an indication of temperature inside the vessel when supported by said frame;
    a heating system that heats the vessel when supported by said frame; and
    a control system coupled to said temperature sensor and said heating system and that controls said heating system to regulate temperature inside the vessel when supported by said frame.

13. A dissolution tester, comprising:
a frame that operatively supports a vessel having an interior into which a tablet is placed for testing dissolution of the tablet;
a shaft assembly supported by said frame and including a shaft having an end that extends into the interior of the vessel when the vessel is supported by said frame; and
an imaging system having first and second cameras that face one another in a vertical orientation with said first camera positioned in said shaft to image an area below said shaft and between said shaft and the vessel when supported by said frame and said second camera imaging the area below said shaft and between said shaft and the vessel when supported by said frame from a position below the vessel when supported by said frame to thereby image a tablet when present in the area below said shaft and between said shaft and the vessel when supported by said frame from two directions.

14. The tester of claim 13, wherein said first camera is oriented to image downward through a bottom of said shaft in order to obtain images of the area below said shaft and between said shaft and the vessel when supported by said frame, and said second camera is positioned on said frame at a location that will be directly below the vessel when the vessel is supported by said frame and oriented to image upward toward the bottom of the vessel when supported by said frame.

15. The tester of claim 14, further comprising:
a disk of transparent material arranged on said shaft below said first camera, said disk of transparent material forming part of the bottom of said shaft such that said first camera obtains images of the area below said shaft and between said shaft and the vessel when supported by said frame through said disk of transparent material;
a control system coupled to said first and second cameras for controlling imaging by said first and second cameras;
a recording unit that records images being obtained by said first and second cameras; and
a monitor coupled to said first and second cameras for displaying images obtained by said first and second cameras.

16. The tester of claim 14, further comprising an attachment attached to the end of said shaft that extends into the interior of the vessel when the vessel is supported by said frame, said attachment being selected from a paddle and a basket.

17. The tester of claim 1, wherein said integral imaging system further comprises a second camera fixed to said frame in a position underneath the vessel when the vessel is supported by said frame and oriented to image upward toward a bottom of the vessel.

18. The tester of claim 14, wherein said imaging system further comprising a tube arranged in a hollow portion of said shaft, said first camera being mounted into said tube such that said first camera is in said hollow portion of said shaft, said first camera imaging the area below said shaft and between said shaft and the vessel when supported by said frame from a position of said first camera in said hollow portion of said shaft.

19. The tester of claim 17, wherein said frame includes a bottom plate, further comprising a mount tube in which said second camera is housed, said mount tube being mounted to said bottom plate.

20. The tester of claim 19, further comprising a cap with a seal arranged over said second camera and a lens cover arranged over an imaging aperture of said second camera.

* * * * *